US010478106B2

(12) United States Patent
Perez Calero et al.

(10) Patent No.: US 10,478,106 B2
(45) Date of Patent: Nov. 19, 2019

(54) PROBE, SYSTEM, AND METHOD FOR NON-INVASIVE MEASUREMENT OF BLOOD ANALYTES

(71) Applicant: Nederlandse Organisatie voor toegepast-natuurwetenschappelijk onderzoek TNO, s-Gravenhage (NL)

(72) Inventors: Daniel Perez Calero, The Hague (NL); James Peter Robert Day, The Hague (NL); Jacobus Thomas Wilhelmus Elisabeth Vogels, The Hague (NL); Maarten J. Scholtes-Timmerman, The Hague (NL); Jacobus Johannes Frederik van Veen, The Hague (NL)

(73) Assignee: Nederlandse Organisatie voor toegepast-natuurwetenschappelijk onderzoek TNO, 's-Gravenhage (NL)

(*) Notice: Subject to any disclaimer, the term of this patent is extended or adjusted under 35 U.S.C. 154(b) by 594 days.

(21) Appl. No.: 15/026,312

(22) PCT Filed: Oct. 1, 2014

(86) PCT No.: PCT/NL2014/050677
§ 371 (c)(1),
(2) Date: Mar. 31, 2016

(87) PCT Pub. No.: WO2015/050444
PCT Pub. Date: Apr. 9, 2015

(65) Prior Publication Data
US 2016/0235345 A1 Aug. 18, 2016

(30) Foreign Application Priority Data
Oct. 2, 2013 (EP) .................................. 13187155

(51) Int. Cl.
*A61B 5/1455* (2006.01)
*A61B 5/00* (2006.01)
(Continued)

(52) U.S. Cl.
CPC .......... *A61B 5/1455* (2013.01); *A61B 5/0075* (2013.01); *A61B 5/1451* (2013.01);
(Continued)

(58) Field of Classification Search
CPC . A61B 5/1455; A61B 5/1451; A61B 5/14546; A61B 5/0075; A61B 5/14532;
(Continued)

(56) References Cited

U.S. PATENT DOCUMENTS 5,815,260 A * 9/1998 Dou ..................... A61B 10/007
356/301
5,842,995 A 12/1998 Mahadevan-Jansen et al.
(Continued)

FOREIGN PATENT DOCUMENTS

WO 2011/083111 A1 7/2011

OTHER PUBLICATIONS

Nov. 20, 2014—International Search Report and Written Opinion of PCT/NL2014/050677.

*Primary Examiner* — Eric F Winakur
*Assistant Examiner* — Abid A Mustansir
(74) *Attorney, Agent, or Firm* — Banner & Witcoff, Ltd.

(57) ABSTRACT

The present disclosure concerns a measuring probe (10) for non-invasive in vivo measurement of blood analytes (33) by Raman spectroscopy. The measuring probe (10) comprises a housing (20) having a skin engaging surface (21). The housing (20) comprises a first optical system (1, 3, 4) arranged for providing source light (11) to the skin engaging surface (21) for penetrating a subject's skin (31) by said source light (11) for interacting with the blood analytes (33).

(Continued)

The housing (20) further comprises a second optical system (5, 6, 2) arranged for capturing scattered Raman light (12) from the blood analytes (33) for measurement of the blood analytes (33). The first optical system (1, 3, 4) is arranged for providing the source light (11) as a collimated beam (1*c*) onto the skin (31).

15 Claims, 4 Drawing Sheets

(51) Int. Cl.
    *A61B 5/145*     (2006.01)
    *G01N 21/65*     (2006.01)
    *A61B 90/30*     (2016.01)

(52) U.S. Cl.
    CPC ...... *A61B 5/14532* (2013.01); *A61B 5/14546* (2013.01); *A61B 5/14551* (2013.01); *A61B 5/6847* (2013.01); *A61B 2090/306* (2016.02); *A61B 2503/40* (2013.01); *A61B 2562/0238* (2013.01); *A61B 2562/185* (2013.01); *A61B 2576/00* (2013.01); *G01N 21/65* (2013.01)

(58) Field of Classification Search
    CPC .............. A61B 5/14551; A61B 5/6847; A61B 2090/306; A61B 2562/185; A61B 2562/0238; A61B 2503/40; A61B 2576/00; G01N 21/65
    See application file for complete search history.

(56) References Cited

U.S. PATENT DOCUMENTS

| | | | |
|---|---|---|---|
| 6,303,934 B1 * | 10/2001 | Daly | G01J 3/02 |
| | | | 250/339.02 |
| 6,483,581 B1 * | 11/2002 | Ben-Amotz | G01J 3/02 |
| | | | 356/301 |
| 7,873,397 B2 | 1/2011 | Higgins et al. | |
| 8,515,506 B2 | 8/2013 | Ridder et al. | |
| 2006/0178570 A1 * | 8/2006 | Robinson | A61B 5/14558 |
| | | | 600/310 |
| 2009/0073439 A1 * | 3/2009 | Tearney | A61B 5/0075 |
| | | | 356/337 |
| 2010/0168586 A1 * | 7/2010 | Hillman | G02B 23/2476 |
| | | | 600/476 |
| 2013/0018237 A1 * | 1/2013 | Henneberg | A61B 5/0059 |
| | | | 600/310 |
| 2015/0164336 A1 * | 6/2015 | Mahadevan-Jansen | A61B 5/0091 |
| | | | 600/477 |

* cited by examiner

PROBE, SYSTEM, AND METHOD FOR NON-INVASIVE MEASUREMENT OF BLOOD ANALYTES

CROSS-REFERENCE TO RELATED APPLICATIONS

This application is a U.S. National Stage application under 35 U.S.C. § 371 of International Application PCT/NL2014/050677 (published as WO 2015/050444 A1), filed Oct. 1, 2014, which claims priority to Application EP 13187155.0, filed Oct. 2, 2013. Benefit of the filing date of each of these prior applications is hereby claimed. Each of these prior applications is hereby incorporated by reference in its entirety.

TECHNICAL FIELD AND BACKGROUND

The present disclosure relates to a measuring probe, system, and method for non-invasive in vivo measurement of blood analytes by Raman spectroscopy.

For many applications it can be desirable to measure a concentration of blood analytes of a patient. For example, diabetic patients may benefit from a frequent measurement of glucose concentration in the blood to determine a state of health. However, traditional invasive measurements such as blood puncture and extraction can be stressful and painful over time and may give rise to health risks (e.g. infection). A non-invasive device for the measurement of blood analytes, such as glucose, is therefore desirable.

For example, international application WO 2011/083111 describes an apparatus for non-invasive in vivo measurement by Raman spectroscopy of glucose present in interstitial fluid in the skin of a subject. The apparatus comprises a measuring probe that receives light from a light source through a first fibre. The incoming light illuminates and interacts with the skin. Raman light received back from the skin, is collected by the probe and sent via a second fibre to a spectrometer connected to a computer for subsequent analysis of the spectral components. In the apparatus, optical components defining a return path for Raman scattered light selectively transmit light scattered from near a measurement location such that at least 50% of Raman scattered light received at the light detection unit originates at depths from 60 to 400 µm beyond a distal surface of the skin engaging probe. By the confocal configuration of the probe, the Raman light arises solely from interactions between the incoming light and the skin at the focus spot; hence contributions from the cone-like areas above and below the focus spot are minimized or eliminated.

For example, U.S. Pat. No. 7,873,397 describes another spectroscopic optical system for Raman spectroscopy to measure a blood and/or tissue analyte, wherein light that penetrates the target is collected from a region on the target's surface that is not directly illuminated. To this end, the collection optics preferably are placed directly in contact with the target or at least significantly close to the target. Light that illuminates the target is in a pattern that partially but not completely surrounds the region from which the portion of the light that penetrates the target is collected.

For example, US 2013/0018237 describes a different apparatus for non-invasive in vivo measurement by Raman spectroscopy wherein illumination light is focussed by a lens on the skin and Raman light is collected through the same lens. The Raman light is wavelength separated from the illumination light using a dichroic mirror.

For example, U.S. Pat. No. 8,515,506 describes methods for noninvasive determination of in vivo alcohol concentration using Raman spectroscopy. In the method, source and receiver fibres are placed against a tissue sampling surface.

Unfortunately, measurement of blood analyte concentrations by known, Raman-based reflection probes can be very sensitive to the exact positioning of the probe on the skin, thus making the known probes difficult to operate and less reproducible. Also, measurements by the known probes can lead to different results for different patients even when these patients have the same analyte concentration in their blood, thus requiring patient-specific calibration.

Accordingly, there is a desire for an improved measurement probe and system for non-invasive in vivo measurement of blood analytes by Raman spectroscopy that is easy to operate to provide reproducible results.

SUMMARY

The present disclosure provides a measuring probe for non-invasive in vivo measurement of blood analytes by Raman spectroscopy. The measuring probe comprising a housing having a skin engaging surface. The housing comprising a first optical system arranged for providing source light to the skin engaging surface for penetrating a subject's skin by said source light for interacting with the blood analytes. The housing further comprises a second optical system arranged for capturing scattered Raman light from the blood analytes. The first optical system is arranged for providing the source light as a collimated beam onto the skin.

A collimated beam penetrates uniformly into the skin up to a depth that is determined by the penetration depth of the light, e.g. based on the scattering properties of the medium and not by any specific focal distance of the apparatus. A tissue volume irradiated by the collimated beam is therefore less dependent on a predefined distance with respect to the probe geometry and more dependent on intrinsic properties of the probe light and skin. Furthermore, a collimated beam provides a more homogeneous irradiation of the skin than a focused beam. Accordingly, by providing the source light as a collimated beam onto the skin, the measuring probe can be relatively insensitive to exact placement of the probe. In contrast, it is noted that the previously known confocal measurement probes collect Raman light from a small tissue volume located at a specific distance with respect to the probe geometry. However, such a localized measurement can be very sensitive to a positioning of the probe, e.g. orientation, location, and applied pressure, because the focal volume is both very small and only defined relative to the probe geometry. Moreover, the results can vary depending on skin composition (e.g. thickness and type) that can vary between different locations of the body and between different individuals. Accordingly, the presently disclosed measurement probe that provides the source light as a collimated beam onto the skin, can have a reduced sensitivity to the placement of the probe and/or reduced patient-specificity. This makes the currently disclosed probe easier to operate and provides more reproducible results.

By providing the collimated beam at an oblique incidence angle, the light traverses a longer path length before deeply penetrating the skin. The beam is therefore better absorbed in the upper layers of the skin to produce a Raman signal. Also because the Raman signal is not produced at great depth, the signal can be more efficiently collected, e.g. better escape the skin to reach the probe again. Also, a relatively large skin area can be illuminated by the collimated beam at an oblique angle, due to the larger spot size. Preferably an illuminated skin area is more than 5 mm$^2$, more than 10 mm$^2$, more than 20 mm$^2$, more than 40 mm$^2$, e.g. between 5 and 100 mm$^2$. A larger illuminated area may correspond to a reduced sensitivity of the probe with respect to placement and/or reduced patient-specificity.

By spatially separating the scattered Raman light from a specular reflection of the collimated beam, requirements for a wavelength filter (e.g. a notch filter arranged for passing the Raman light and rejecting the source light) can be less stringent or the wavelength filter can be omitted entirely. Spatial separation can be enhanced by the oblique incidence angle of the source light. By arranging an entrance of the second optical system outside a path of the specular reflection, it can be prevented that the specular reflection enters the second optical system. By virtue of the spatial separation, a majority of the Raman light can be collected from the illuminated region of the skin. This may improve e.g. signal-to-noise ratio. Advantageously, it is not necessary to limit the detected Raman light to a region that is not directly illuminated such as the prior art system of U.S. Pat. No. 7,873,397. For example, the collection optics do not need to be placed directly against the skin. The illuminated area can also be larger than the prior art, since it is not limited to an edge region surrounding the collection area. This may also provide reduced sensitivity of the probe with respect to placement and/or reduced patient-specificity. Also a depth range of the skin from which the Raman light is collected can be different.

A convenient way of providing a collimated beam of source light to the probe can be an optical fibre bundle. The collimated beam can be projected onto the skin, e.g. by the fibre bundle or further light guiding optics such as mirrors, (collimating) lenses, etc.

By projecting the illuminated spot of the skin onto an optical fibre bundle, a relatively large light spot can be captured and with large acceptance angles, e.g. compared to a single fibre. Having a wide cross-section optical fibre bundle can thus improve light efficiency.

The present measuring probe can be comprised in a measuring system for non-invasive in vivo measurement of blood analytes by Raman spectroscopy. The system typically comprises one or more of a light source, a spectrometer, a photodetector, and/or a processor for performing respective tasks. For example, the light source is arranged for providing the source light to the measuring probe. The spectrometer is arranged for receiving the Raman light from the measuring probe and projecting a Raman spectrum of the Raman light on a photodetector. Furthermore, the photodetector is arranged for measuring the projected Raman spectrum. Furthermore, the processor is arranged for reading out measurement data from the photodetector and calculating a presence and/or concentration of the blood analytes based on the measured Raman spectrum. For example, the system can be arranged for detecting glucose as blood analytes.

By providing a monochromatic light source, a clear Raman signal can be produced. By using a monolithic spectrometer, a more compact and robust system can be provided, e.g. a portable system. By using a flexible connection between the measuring probe and the light source and/or to the spectrometer, the measuring probe can be substantially free to move and/or rotate with respect to the light source and/or spectrometer. For example, the flexible connection can be provided by optical fibres allowing the probe to move within a range of the fibres therein between. To increase light efficiency, an optical fibre bundle can be arranged in a circular input pattern matching a projection of the illuminated measuring spot. Advantageously, another end of the fibre bundle can be provided with an elongate line pattern to provide a desired input for a spectrometer.

It is found that a Raman signal measured from a large tissue volume can be accompanied by a relatively large background signal (compared to confocal measurements) that can consist of both time-dependent and constant background features. The inventors find that more reliable results can be provided by pre-processing the measurement data for subtracting a background. It is found particularly advantageous to utilize a combination of time-dependent noise suppression and subtraction of a modelled constant background. For example, EMSC, wavelets or convex hull algorithms can be used. Alternatively or in addition, the background can be modelled by polynomial fitting, e.g. spline fitting. Alternatively or in addition to the pre-processing, a concentration dependent signal such as a glucose concentration can be extracted from the measurement data by techniques such as multi-variate regression.

In one aspect, the present disclosure relates to a method for non-invasive in vivo measurement of blood analytes by Raman spectroscopy, the method comprising providing source light for penetrating a subject's skin for interacting with the blood analytes; and capturing scattered Raman light from the blood analytes for measurement of the blood analytes; wherein the source light is provided as a collimated beam onto the skin. The method can provide similar advantages as the probe and/or system.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
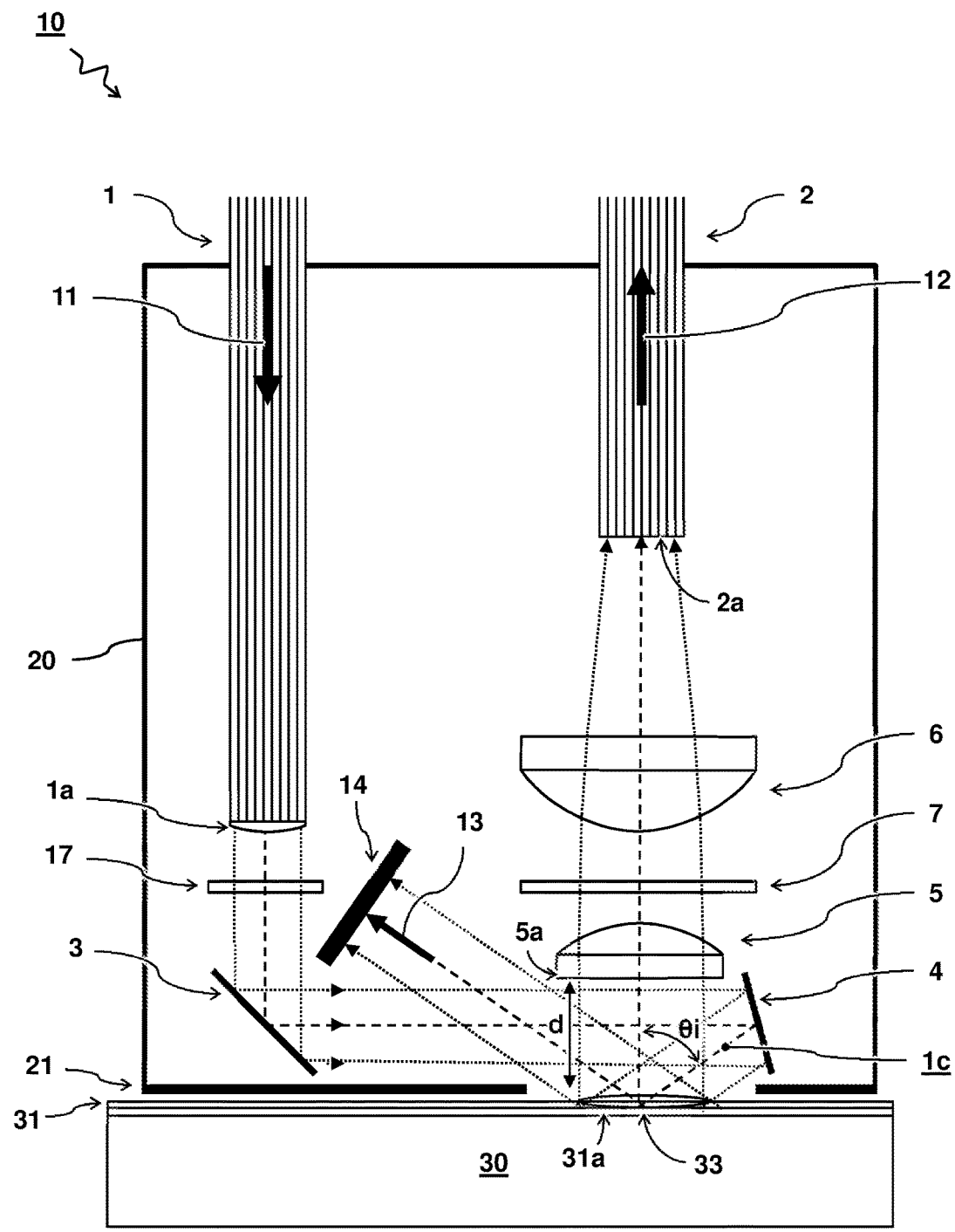
FIG. 1 shows a schematic cross-section illustration of a measuring probe.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 shows a schematic cross-section illustration of a measuring probe 10 for non-invasive in vivo measurement of blood analytes 33 by Raman spectroscopy. The measuring probe 10 comprises a housing 20 having a skin engaging surface 21. The housing 20 comprises a first optical system 1,3,4 arranged for providing source light 11 to the skin engaging surface 21 for penetrating the skin 31 of a subject 30 by said source light 11. The source light 11 is suitable for interacting with the blood analytes 33 to produce scattered Raman light 12. The housing 20 further comprises a second optical system 5,6,2 arranged for capturing the scattered Raman light 12 from the blood analytes 33. The captured Raman light 12 can be used to measure the presence and/or concentration of the blood analytes 33. The term 'capture' is used to describe the light that successfully enters the optical system to measure the light.

Advantageously, the first optical system 1,3,4 is arranged for providing the source light 11 as a collimated beam 1c onto the skin 31. Collimated light is light whose rays are substantially parallel, and therefore will spread minimally as it propagates. It will be understood that while ideally, the rays of a collimated beam are collinear and do not disperse with distance, in reality, some dispersion, e.g. as a result of diffraction may be tolerated. A collimated beam may exhibit a substantially constant intensity profile as a function of distance. This may be contrasted with a converging beam whose intensity increases towards a focus (e.g. used in confocal microscopy) or a diverging beam whose intensity drops away from the focus. A beam may be considered collimated if the beam does not considerably converge or diverge over a distance between a source and a target. Depending on context (e.g. scale), this may be quantified e.g. by looking at the angles between rays of light in a beam. In one example, the angles between rays of light in a collimated beam are within a threshold value of 10 degrees, preferably even lower, e.g. 5 degrees or even 1 degree. The more collimated the beam, the less the intensity profile will change over distance. In one embodiment, a collimating element 1a is provided in an optical path between the first optical fibre bundle 1 and the skin engaging surface 21. For example, in one embodiment, the first optical fibre bundle 1 comprises a collimating output lens 1a.

In one embodiment, the first optical system 1,3,4 is arranged to provide the collimated beam 1c at an oblique incidence angle $\theta i$ with respect to a normal of the skin engaging surface 21. Preferably, the incidence angle $\theta i$ is larger than 45 degrees, more preferably larger than 50 degrees, e.g. 60 degrees with respect to a surface normal of the skin 31 or skin engaging surface 21.

In one embodiment, the second optical system 5,6,2 is arranged for spatially separating the scattered Raman light 12 from a specular reflection 13 of the collimated beam off a surface of the skin 31 when the skin engaging surface 21 engages the skin 31. Specular reflection is the reflection of light from a surface, in which light from a single incoming direction (a beam or ray) is reflected into a single outgoing direction. Such behaviour is described e.g. by the law of reflection, which states that the direction of the incident light, and the direction of the reflected light have the same angle with respect to the surface normal, i.e. the angle of incidence equals the angle of reflection. Furthermore, the incident, normal, and reflected directions are coplanar. Specular reflection can be contrasted e.g. with diffuse reflection or scattering, wherein incident light is reflected or scattered in a broad range of directions. Physical surfaces (such as skin) may exhibit a combination of specular and diffuse reflections, e.g. a first portion of the reflected light may be specular (i.e. having the same angle with respect to the surface normal as the incident light) and a second portion of the reflected light may be diffuse (i.e. having a more isotropic distribution). The distribution of specular and diffuse light may be dependent e.g. on a roughness and material of the surface and/or an angle of incidence and wavelength of the light.

In one embodiment, the second optical system, e.g. collection optics 5a, is configured such that all or at least a majority of the captured scattered Raman light 12 from the blood analytes 33 emanates from the illuminated surface 31a of the skin. Preferably, an entrance 5a of the collection optics 5 of the second optical system are distanced from the skin engaging surface 21 and thus the illuminated surface 31a of the skin. By distancing the collection optics from the skin engaging surface 21, it can be easier to have the beam 1c illuminate the underneath surface 31a unobstructed by the said collection optics. Accordingly, the collection optics (e.g. optical surface through which practically all light enters the second optical system, e.g. surface of a collection lens or fibre entrance) of the second optical system are preferably at a distance of more than a few millimetres from the skin engaging surface (measured for example perpendicular to the skin engaging surface). For example, the distance is preferably more than two millimetres, preferably more than three millimetres of even more than five millimetres, e.g. between three and ten millimetres. Advantageously, by distancing the collection optics 5 from the skin engaging surface 21, a beam of light can optionally be passed underneath the collection optics 5a and reflected by a mirror 4 adjacent or at least close to the collection optics. In this way, a compact arrangement is provided. As a further advantage, the optical components can be more easily kept clean.

Alternatively, or in addition, by increasing the illumination angle θi, the collection optics 5a may be closer while at the same time increasing the illuminated area. Accordingly, the collimated beam 1c is preferably provided at an oblique incidence angle θi with respect to a normal of the skin 33 or skin engaging surface. For example, the incidence angle θi is preferably, more than 45 degrees, more than 50 degrees, or even more 60 degrees, e.g. between 45 and 85 degrees.

Preferably, an entrance 5a of the second optical system 5,6,2 is arranged outside a path of the specular reflection 13 for preventing said specular reflection 13 from entering the second optical system 5,6,2. By preventing the specular reflection from entering the second optical system, it may be at least partially prevented that the source light 11 overwhelms the Raman light 12. Additionally, an optional filter 7 may be provided. For example a notch filter with a narrow stop band centred on a wavelength of the source light can be used to filter any remaining (diffuse or stray) source light while passing the Raman light 12.

In one embodiment, the first optical system 1,3,4 comprises a first optical fibre bundle 1 and light guiding optics 3,4. The first optical fibre bundle 1 is arranged for projecting a collimated beam 1c onto the light guiding optics 3,4, and the light guiding optics 3,4 are arranged to project the collimated beam 1c onto the skin 31. In the present embodiment, the light guiding optics 3,4 comprise a pair of mirrors. Also other optics such as parabolic mirrors can be used with similar result. The lenses may even be completely omitted, i.e. relying only on the optical fibre to capture the Raman light. In one embodiment, the first optical system comprises an optional band pass filter 17 for cleaning up the source light 11.

In one embodiment, the second optical system 5,6,2 comprises imaging optics 5,6 and a second optical fibre bundle 2. The collimated beam 1c irradiates the skin 31 resulting in an illumination pattern. The second optical system 5,6,2 is arranged to project an image of the illuminated pattern onto an entrance 2a of the second optical fibre bundle 2.

Preferably, the measuring probe is arranged for measuring blood analytes in the interstitial fluid of the skin. Interstitial fluid, also known as tissue fluid, is a solution that bathes and surrounds the cells of multicellular organisms. It is the main component of the extracellular fluid, which also includes plasma and transcellular fluid. The interstitial fluid is found in interstitial spaces, also known as the tissue spaces. Interstitial fluid typically consists of a water solvent containing blood analytes such as sugars, salts, fatty acids, amino acids, coenzymes, hormones, proteins/peptides, neurotransmitters, as well as waste products from the cells. The composition of tissue fluid depends upon the exchanges between the cells in the biological tissue and the blood. Tissue fluid may also contain some types of white blood cell, which help combat infection. Interstitial fluid and blood are not the same because not all of the contents of the blood pass into the tissue. For example, red blood cells, platelets, and plasma proteins of the blood may not pass through the walls of the capillaries. It will be appreciated that an analysis of the composition of interstitial fluid or blood can provide valuable information, e.g. on the health of the body and/or specific tissues. The analysis may comprise measurement of the presence and/or concentration of one or more of the above identified blood analytes in the interstitial fluid or blood. For example, measuring a glucose concentration in the interstitial fluid of the skin may provide valuable information on the health status of diabetic patients as this reflects the value for the concentration in blood.

Preferably, the measurement of the blood analytes is performed by Raman spectroscopy. Raman spectroscopy is a spectroscopic technique that is used to observe vibrational, rotational, and/or other low-frequency modes in a sample, in this case e.g. interstitial fluid comprising blood analytes. The technique is said to rely on inelastic scattering, or Raman scattering, of an incoming light beam, usually a monochromatic light beam, usually from a laser in the visible, near infrared, or near ultraviolet range. The term 'light' as used herein includes all forms of electromagnetic radiation such as visible, infrared and/or ultraviolet radiation. The light beam interacts with molecular vibrations, phonons or other excitations in the sample, resulting in the energy of the photons in the scattered light being shifted up or down. The shift in energy of the scattered light with respect to that of the incoming beam can give information about the vibrational modes in the system and/or be used to analyse the system, e.g. determine the presence and/or concentration of an analyte. In one embodiment, the light source is arranged to emit light having a wavelength in a range of 700 nm to 1050 nm.

Since the scattered light, carrying the Raman signal, can in principle leave the tissue in all directions, a detector and/or light guides (e.g. lenses, mirrors, fibres) that collect and/or carry the scattered light back to the detector, may be placed at any accessible angle. In the present arrangement, the light guide is advantageously positioned in a backscattering configuration in the same probe that provides the incident light. In this way a compact and easy to handle instrument is provided. The scattered radiation that is captured from the sample, is usually sent through a dispersing and/or diffracting element such as a monochromator or spectrometer to select a specific wavelength or range of wavelengths. Typical monochromators or spectrometers may comprise a wavelength resolving element such as a prism and/or diffraction grating. E.g. by adjusting an angle of the grating, it can be controlled which wavelengths of scattered radiation reach a detecting element, e.g. a photo detector arranged for measuring an intensity of light falling on the detecting element. The detecting element itself can e.g. be a single pixel detector or a multi-pixel array detector such as a charge-coupled device (CCD), which allows simultaneous measuring of the spectrum at multiple wavelengths.

The embodiments described herein can be advantageously used in corresponding methods. One method for non-invasive in vivo measurement of blood analytes 33 by Raman spectroscopy comprises providing source light 11 for penetrating a subject's skin 31 for interacting with the blood analytes 33; and capturing scattered Raman light 12 from the blood analytes 33 for measurement of the blood analytes 33; wherein the source light 11 is provided as a collimated beam 1c onto the skin 31. In embodiment, the collimated beam 1c is provided at an oblique incidence angle θi with respect to a normal of the skin 33. In one embodiment the scattered Raman light 12 is spatially separated from a specular reflection 13 of the collimated beam off a surface of the skin 31. In one embodiment, an entrance 5a of an optical system 5,6,2 for capturing the Raman light 12 is arranged outside a path of the specular reflection 13 for preventing said specular reflection 13 from entering the entrance 5a.

Figure 2:
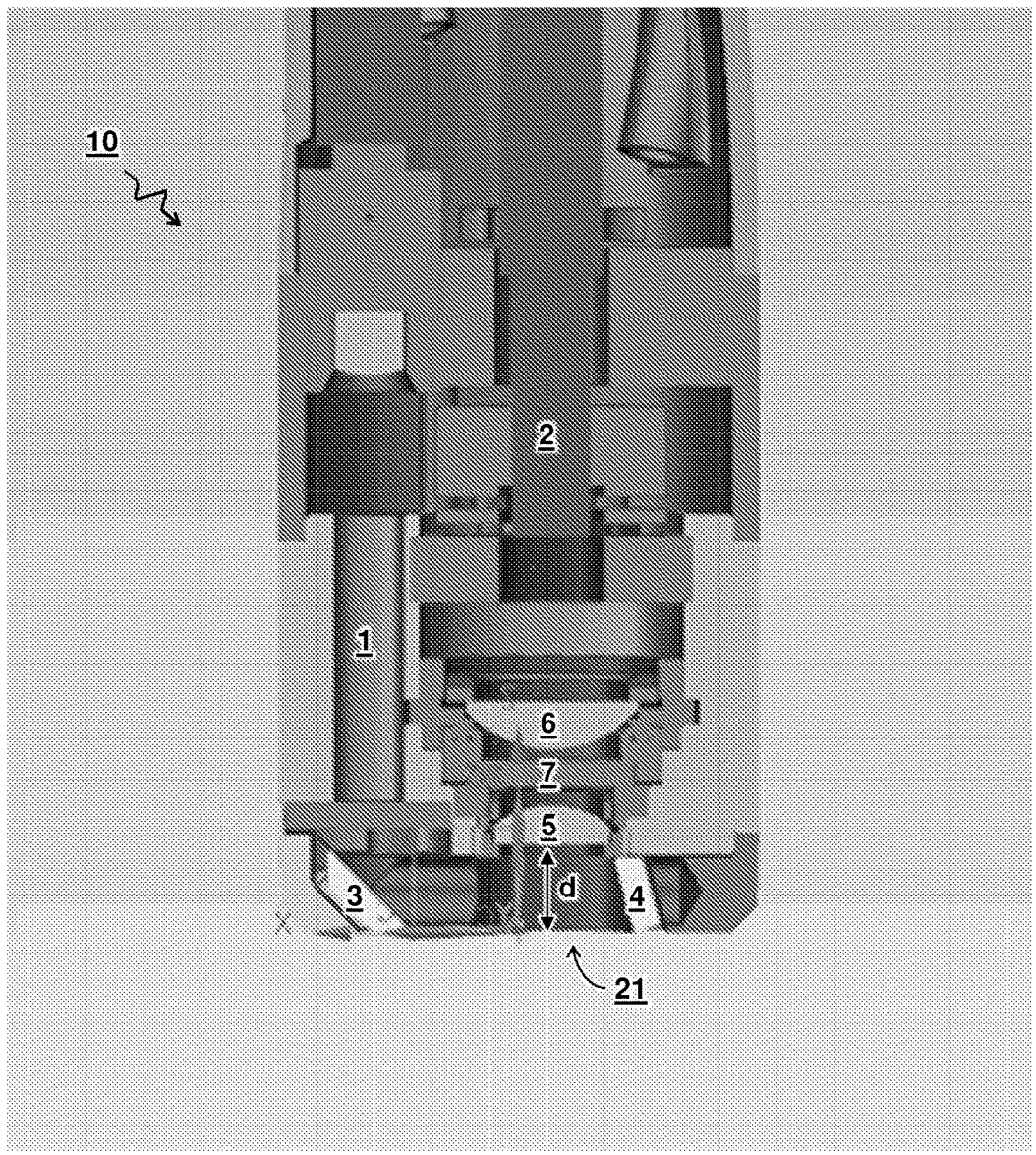
FIG. 2 shows another schematic cross-section illustration of the measuring probe.

FIG. 2 shows a schematic cross-section illustration of an embodiment of the measuring probe 10. The figure shows a first optical fibre bundle 1 leading the source light to mirrors 3 and 4 which irradiate the skin via skin engaging surface 21.

Resulting Raman light enters the second optical system comprising lenses 5 and 6, and second optical fibre bundle 2. Also an optional filter 7 is shown.

Figure 3:
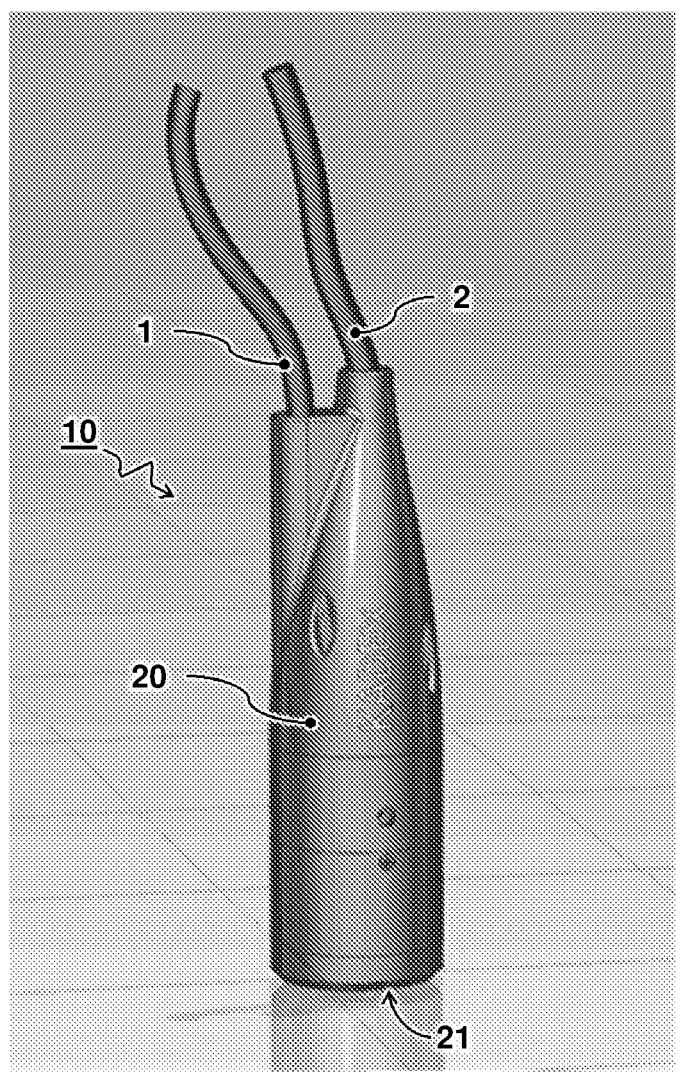
FIG. 3 shows a side view of the measuring probe.

FIG. 3 shows a side view of an embodiment of the measuring probe 10. Optical fibre bundles 1 and 2 lead the source and Raman light to and from the skin engaging surface 21 by means of optical components in the housing 20.

Figure 4:
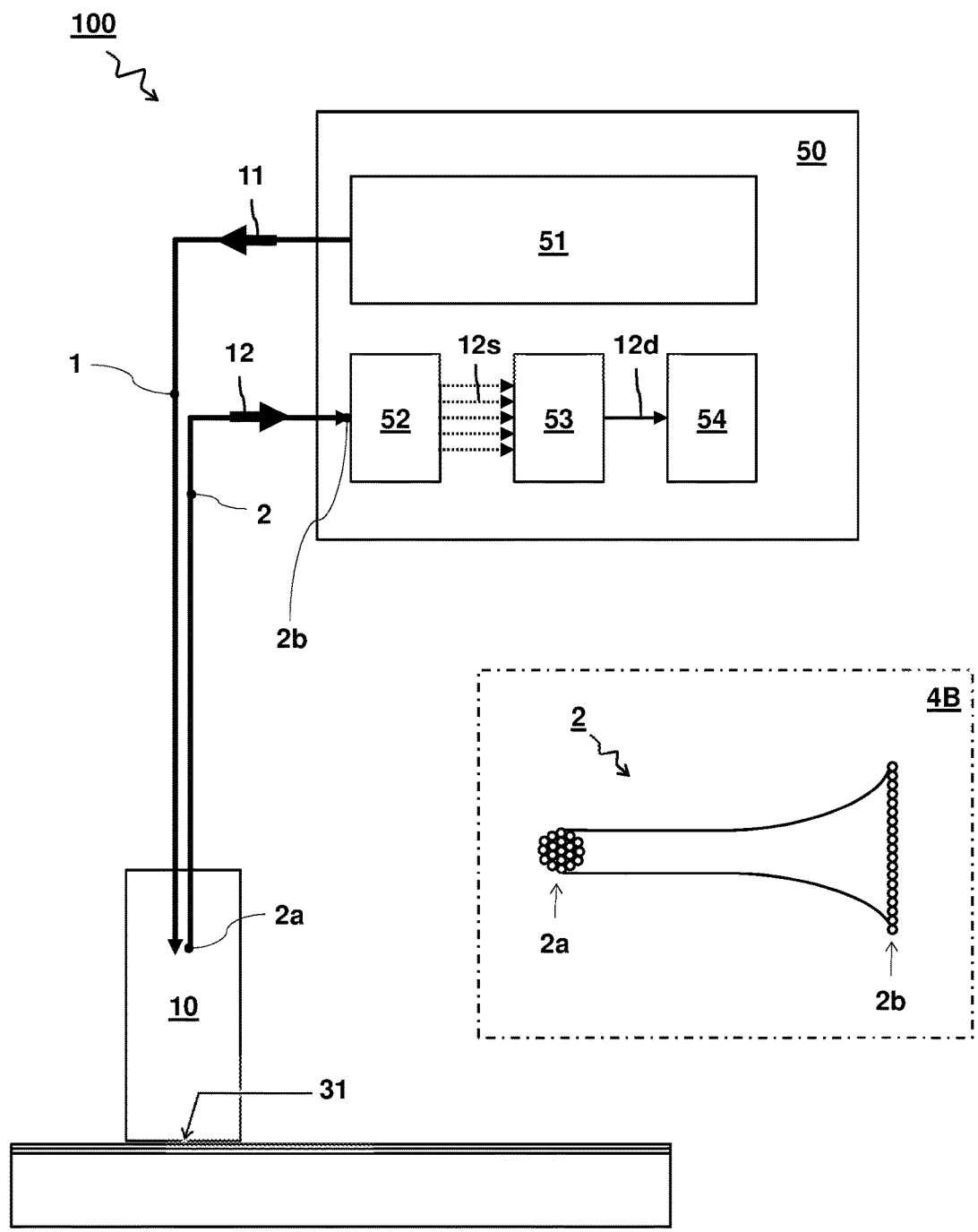
FIG. 4 shows a schematic illustration of a measuring system.

FIG. 4 shows a schematic illustration of a measuring system 100 for non-invasive in vivo measurement of blood analytes 33 by Raman spectroscopy. The measuring system 100 e.g. comprises a measuring probe 10 as describe herein. The measuring system 100 further comprises a light source 51, a spectrometer or monochromator 52, a camera or photodetector 53, and a processor 54.

The light source 51 is arranged for providing the source light 11 to the measuring probe 10. The spectrometer 52 is arranged for receiving the Raman light 12 from the measuring probe 10 and projecting a Raman spectrum 12s of the Raman light 12. The sensor 53 is arranged for measuring the projected Raman spectrum 12s. The processor 54 is arranged for reading out measurement data 12d from the photodetector 53 and calculating a presence and/or concentration of the blood analytes 33 based on the measured Raman spectrum 12s.

In one embodiment, the system is arranged for detecting glucose as blood analytes 33. Accordingly, a versatile glucose measuring device is provided.

In one embodiment, the measuring probe 10 is connected to the light source 51 and/or spectrometer 52 by flexibly moveable optical fibres 1,2. Accordingly, the measuring probe 10 is substantially free to move and/or rotate with respect to the light source 51 and/or spectrometer 52 within a range of the optical fibres 1,2 therein between.

In one embodiment, an optical path between a measuring spot on the skin 31 and the spectrometer 52 is connected by an optical fibre bundle 2. As shown in the inset 4B, an input end 2a of the fibre bundle 2 is shaped in a circular pattern to receive a projection of the measuring spot and an output end 2b of the fibre bundle 2 is shaped as an elongate line pattern to provide input to the spectrometer 52. In this way a slit or line-like illumination pattern can be provided to the spectrometer 52.

In one embodiment, the processor 54 is arranged for pre-processing the measurement data 12d for subtracting a background. For example, the pre-processing comprises a combination of time-dependent noise suppression and subtraction of a modelled constant background. For example, the constant background is modelled by polynomial fitting. For example, the background can be modelled by spline fitting. In mathematics, a spline is a sufficiently smooth polynomial function that is piecewise-defined, and possesses a high degree of smoothness at the places where the polynomial pieces connect (which are known as knots). The smooth polynomial may be advantageously distinguished from 'sharp' spectral features, e.g. the Raman signature of an analyte. In one embodiment, a concentration dependent signal such as for glucose is extracted from the measurement data 12d by a regression technique, e.g. multi-variate regression. Preferably, the data analysis is done by a combination of pre-processing and regression. Pre-processing is preferably done with EMSC, or background correction with wavelets or convex hull. Regression is preferably done with a technique that can cope with both categorical data (e.g. to deal with different skin types) and quantitative data (such as concentrations), e.g. Random Forest.

In one embodiment, the spectrometer 52 is a monolithic spectrometer 52 comprising a body of solid material having optical surfaces arranged to guide the light along an optical path inside the body. The body material is transparent at least to the wavelengths of light for which the spectrometer is intended to be used. For example, depending on the intended use, the material can be transparent to visible, infrared and/or ultraviolet radiation. The body shape comprises optical surfaces to transmit, reflect, shape (e.g. collimate or focus) and refract (e.g. bend or disperse) the light as it travels along the optical path. Optionally, the optical surfaces may be coated, e.g. with a reflective material, or an optical piece such as a mirror or grating can be adhered to the optical surface to provide or aid the optical function of the surface. Advantages of a monolithic spectrometer over a regular spectrometer may include compactness, stability, and/or manufacturability. The monolithic spectrometer design provides an opportunity for miniaturization and cost efficiency wherein so-called point-of-care measurements can be performed.

One design of a monolithic spectrometer comprises an entry surface, a collimating surface, a grating surface, a focusing surface, and an exit surface. The entry surface is arranged to receive the light to enter into the body directed along a first part of the optical path. The collimating surface is arranged to receive the entering light directed along the first part of the optical path and to reflect said entering light as a collimated beam directed along a second part of the optical path. The grating surface is arranged to receive the collimated beam directed along the second part of the optical path and to reflect a refracted beam directed along a third part of the optical path according to a wavelength dependent refraction angle. The focusing surface is arranged to receive the refracted beam directed along the third part of the optical path and to focus said refracted beam directed along a fourth part of the optical path for imaging a wavelength component of the light onto a position along a spectral axis in an imaging plane outside the body. The exit surface is arranged in the optical path between the focusing surface and the imaging plane to have the light exit the body.

While example embodiments were thus shown and described for a collimated reflection probe based on Raman spectroscopy, also alternative ways may be envisaged by those skilled in the art having the benefit of the present disclosure for achieving a similar function and result. E.g. optical and electronic systems may be combined or split up into one or more alternative components. The various elements of the embodiments as discussed and shown offer certain advantages, such as ease of use, robustness, and compactness. Of course, it is to be appreciated that any one of the above embodiments or processes may be combined with one or more other embodiments or processes to provide even further improvements in finding and matching designs and advantages. It is appreciated that this disclosure offers particular advantages to analysis of blood analytes through the skin, and in general can be applied for other spectral analysis techniques and analytes in particular the measurement of analytes in scattering media. Applications may include point-of-care instruments for diabetics. For example, in one aspect, the present disclosure provides an instrument (including measuring probe and spectrometer) and method based on Raman spectroscopy with which the glucose concentration in interstitial fluid can be measured through the skin. The measurement can be performed by the patient without requiring difficult clinical processes. The instrument may also be applied to other clinical parameters (cholesterol, triglycerides, alcohol, drugs), and possibly also for veterinary applications.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A measuring probe for non-invasive in vivo measurement of blood analytes by Raman spectroscopy, the measuring probe comprising a housing having a skin engaging surface for engaging a subject's skin, the housing comprising:
   a first optical system comprising light guiding optics configured to direct source light, as a collimated beam, to the skin engaging surface and further configured to cause penetration of the subject 'skin with said collimated beam, for interacting of the collimated beam with the blood analytes, wherein angles between rays of light in the collimated beam are within a threshold value of 10 degrees; and
   a second optical system configured to collect scattered Raman light, obtained from scattering of the collimated beam by the blood analytes, for use in measurement of the blood analytes;
      wherein the first optical system is configured to direct the collimated beam at an oblique incidence angle with respect to a normal incidence angle of the skin engaging surface; and
      wherein the second optical system is configured to spatially separate the scattered Raman light from a specular reflection of the collimated beam from the subject's skin.

2. The measuring probe according to claim 1, wherein an entrance of the second optical system is arranged outside a path of the specular reflection for preventing said specular reflection from entering the second optical system.

3. The measuring probe according to claim 2, wherein the entrance of the second optical system is arranged at a distance from the skin engaging surface, wherein the collimated beam of source light is passed by a first mirror underneath collection optics of the second optical system, between the entrance and the skin engaging surface, and reflected by a second mirror adjacent the collection optics at the skin engaging surface as the collimated beam to illuminate a surface of the subject's skin.

4. The measuring probe according to claim 2, wherein the entrance of the second optical system is configured to face towards a surface of the subject's skin that illuminated by said collimated beam, such that at least a majority of the scattered Raman light collected by the second optical system is light that emanates from said surface of the subject's skin, wherein said surface of the subject's skin that is illuminated by side collimated beam has an area of more than 5 mm².

5. The measuring probe according to claim 1, wherein the first optical system comprises a first optical fibre bundle and said light guiding optics, wherein the first optical fibre bundle is configured to project said collimated beam onto the light guiding optics, and the light guiding optics are configured to direct the collimated beam onto the subect's skin.

6. The measuring probe according to claim 1, wherein the second optical system comprises imaging optics and a second optical fibre bundle, wherein the second optical system is configured to project an image of an illuminated pattern on the subject's skin, which is illuminated by the collimated beam, onto an entrance of the second optical fibre bundle.

7. A measuring system for non-invasive in vivo measurement of blood analytes by Raman spectroscopy, the measuring system comprising:
   the measuring probe according to claim 1;
   a light source configured to provide the source light to the measuring probe;
   a spectrometer configured to receive the scattered Raman light from the measuring probe and projecting a Raman spectrum of the scattered Raman light;
   a photodetector configured to measure the Raman spectrum;
   a processor configured to read out measurement data from the photodetector and calculating a presence and/or concentration of the blood analytes based on the Raman spectrum.

8. The measuring system according to claim 7, wherein the measuring probe is connected to the light source and/or spectrometer by flexibly moveable optical fibres wherein the measuring probe is substantially free to move and/or rotate with respect to the light source and/or spectrometer within a range of the optical fibres therein between.

9. The measuring system according to claim 7, wherein an optical path between a measuring spot on the skin and the spectrometer is connected by an optical fibre bundle, wherein an input end of the fibre bundle is shaped in a circular pattern to receive a projection of the measuring spot and an output end of the fibre bundle is shaped as an elongate line pattern to provide input to the spectrometer.

10. The measuring system according to claim 7, wherein the processor is configured to pre-process the measurement data for subtracting a background, wherein the pre-processing comprises a combination of time-dependent noise suppression and subtraction of a modelled constant background.

11. The measuring system according to claim 10, wherein the modelled constant background is modelled by polynomial fitting.

12. The measuring system according to claim 7, wherein a Raman signal is extracted from the measurement data by multi-variate regression.

13. The measuring system according to claim 7, wherein the spectrometer is a monolithic spectrometer comprising a body of solid material having optical surfaces configured to guide the scattered Raman light along an optical path inside the body.

14. The measuring system according to claim 7, wherein the system is arranged for detecting glucose as blood analytes.

15. A method for non-invasive in vivo measurement of blood analytes by Raman spectroscopy, the method comprising:
    directing source light as a collimated beam, using light guiding optics, to penetrate a subject's skin with said collimated beam for interacting of the collimated beam with the blood analytes, wherein angles between rays of light in the collimated beam are within a threshold value of 10 degrees; and
    collecting scattered Raman light, obtained from scattering of the collimated beam by the blood analytes, for use in measurement of the blood analytes;
        wherein the collimated beam is directed at an oblique incidence angle with respect to a normal incidence angle of the subject's skin; and
        wherein the scattered Raman light is spatially separated from a specular reflection of the collimated beam from the subject's skin.

\* \* \* \* \*